US005663070A

United States Patent [19]
Barr et al.

[11] Patent Number: 5,663,070
[45] Date of Patent: Sep. 2, 1997

[54] RECOMBINANT PRODUCTION OF A SOLUBLE SPLICE VARIANT OF THE FAS (APO-1) ANTIGEN, FAS TM

[75] Inventors: Philip J. Barr, Berkeley; John P. Shapiro, Albany; Michael C. Kiefer, Clayton, all of Calif.

[73] Assignee: LXR Biotechnology Inc., Richmond, Calif.

[21] Appl. No.: 152,443

[22] Filed: Nov. 15, 1993

[51] Int. Cl.$^6$ ............ C12N 15/12; C07K 14/715
[52] U.S. Cl. ............ 435/325; 536/23.5; 435/320.1; 435/252.3; 435/254.11; 435/69.1; 435/348; 435/361; 435/358
[58] Field of Search ............ 536/23.5; 435/320.1, 435/240.2, 252.3, 254.11, 69.1

[56] References Cited

FOREIGN PATENT DOCUMENTS

| 0510691 | 4/1992 | European Pat. Off. ........ C12N 15/12 |
| WO 93/04169 | 3/1993 | WIPO . |
| WO 94/08454 | 4/1994 | WIPO . |

OTHER PUBLICATIONS

Wyllie, "Glucocorticoid–induced thymocyte apoptosis is associated with endogenous endonuclease activation" *Nature* (1980) 284:555–556.

Kruman et al. "Apoptosis of murine BW 5147 thymoma cells induced by dexamethasone and γ–irradiation" *J. Cell. Physiol.* (1991) 148:267–273.

Itoh et al., "The polypeptide encoded by the cDNA for human cell surface antigen Fas can mediate apoptosis" *Cell* (1991) 66:233–243.

Krammer et al., "Apoptosis in the APO–1 system" *Apoptosis: The Molecular Basis of Cell Death* (1991) Tomei et al., eds., Cold Spring Harbor Laboratory Press, New York, pp. 87–99.

Oehm et al., "Purification and molecular cloning of the APO–1 cell surface antigen, a member of the tumor necrosis factor/nerve growth factor receptor superfamily" *J. Biol. Chem.* (1992) 267:10709–10715.

Rouvier et al., "Fas involvement in Ca$^2$–independent T cell–mediated cytotoxicity" *J. Exp. Med.* (1993) 177:195–200.

Ogasawara et al., "Lethal effect of the anti–Fas antibody in mice" *Nature* (1993) 364:806–809.

Zhu et al., "Systemic gene expression after intravenous DNA delivery into adult mice" *Science* (1993) 261:209–211.

Zapf et al., "Isolation from adult human serum of four insulin–like growth factor (IGF) binding proteins and molecular cloning of one of them that is increased by IGF I administration and in extrapancreatic tumor hypoglycemia" *J. Biol. Chem.* (1990) 265:14892–14898.

Wu et al., "Autoimmune disease in mice due to integration of an endogenous retrovirus in an apoptosis gene" *J. of Exper. Med.* (1993) 178:461–468.

Kanter et al., "Epidermal growth factor and tumor promoters prevent DNA fragmentation by different mechanisms" *Biochem. Biophys. Res. Comm.* (1984) 118:392–399.

Hsu et al., "Differential expression and ligand binding properties of tumor necrosis factor receptor chimeric mutants" *J. Biol. Chem.* (1993) 268:16430–16436.

(List continued on next page.)

*Primary Examiner*—David L. Fitzgerald
*Attorney, Agent, or Firm*—Morrison & Foerster

[57] ABSTRACT

The invention provides soluble forms of the Fas (Apo-1) protein comprising both the intracellular and extracellular domains of the full-length polypeptide. Exemplified is a naturally-occurring splice variant of the Fas gene, FasΔTM, which lacks the transmembrane domain of the native antigen. DNA encoding the protein, cells expressing the recombinant DNA, and methods of using the protein and DNA are also provided.

8 Claims, 11 Drawing Sheets

OTHER PUBLICATIONS

Suda et al., "Molecular cloning and expression of the Fas ligand, a novel member of the tumor necrosis factor family" *Cell* (1993) 75:1169–1178.

Loenen et al., "The CD27 membrane receptor, a lymphocyte-specific member of the nerve growth factor receptor family, gives rise to a soluble form by protein processing that does not involve receptor endocytosis" *Eur. J. Immunol.* (1992) 22:447–445.

Cheng, J., et al. (1993) *Arthritis of Reheumatism* 36 (9 Suppl.): S76 (Abst. No. 228).

Cheng, J., et al. (1994) *Science* 263 : 1759–62.

Behrmann, I., et al. (1994). *Eur. J. Immunol* 24:3057–62.

Cascino, I., et al. (1995) *J. Immunol.* 154: 2706–13.

Cheng J., et al. (1995) *J. Immunol.* 154: 1239–45.

```
                                  GACGCTTCTGGGAGTGAGGGAAGCGGGTTTACGAGTGACTTGGCTGGAGCCTCAGGGGCGGGCACTGGCACGGA
ACACACCCTGAGGCCAGCCCTGGCTGCCCAGGCCTGCCCAGGCGGAGCTGCCTCTTCTCCCGGGGTTGGTGGAGCCCGCTCAGTACGGAGTTGGGGAA
GCTCTTTCACTTCGGAGGATTGCTCAACAACC

ATG CTG GGC ATC TGG ACC CTC CTA CCT CTG GTT CTT ACG TCT GTT GCT AGA TTA TCG TCC AAA AGT
Met Leu Gly Ile Trp Thr Leu Leu Pro Leu Val Leu Thr Ser Val Ala Arg Leu Ser Ser Lys Ser
                     -10                                              -1 +1

GTT AAT GCC CAA GTG ACT GAC ATC AAC TCC AAG GGA TTG GAA TTG AGG AAG ACT GTT ACT ACA GTT
Val Asn Ala Gln Val Thr Asp Ile Asn Ser Lys Gly Leu Glu Leu Arg Lys Thr Val Thr Thr Val
                10                                    20

GAG ACT CAG AAC TTG GAA GGC CTG CAT CAT GGC CAA TTC TGC CAT AAG CCC TGT CCT CCA GGT
Glu Thr Gln Asn Leu Glu Gly Leu His His Gly Gln Phe Cys His Lys Pro Cys Pro Pro Gly
            30                                40

GAA AGG AAA GCT AGG GAC TGC ACA GTC AAT GGG GAT GAA CCA GAC TGC GTG CCC TGC CAA GAA GGG
Glu Arg Lys Ala Arg Asp Cys Thr Val Asn Gly Asp Glu Pro Asp Cys Val Pro Cys Gln Glu Gly
                                        60                                70

AAG GAG TAC ACA GAC AAA GCC CAT TTT TCT TCC AAA TGC AGA AGA TGT AGA TTG TGT GAT GAA GGA
Lys Glu Tyr Thr Asp Lys Ala His Phe Ser Ser Lys Cys Arg Arg Cys Arg Leu Cys Asp Glu Gly
                                80                                          90
```

FIG. 3A

```
CAT GGC TTA GAA GTG GAA ATA AAC TGC ACC CGG ACC CAG AAT ACC AAG TGC AGA TGT AAA CCA AAC
His Gly Leu Glu Val Glu Ile Asn Cys Thr Arg Thr Gln Asn Thr Lys Cys Arg Cys Lys Pro Asn
                        100                 *                       110

TTT TTT TGT AAC TCT ACT GTA TGT GAA CAC TGT GAC CCT TGC ACC AAA TGT GAA CAT GGA ATC ATC
Phe Phe Cys Asn Ser Thr Val Cys Glu His Cys Asp Pro Cys Thr Lys Cys Glu His Gly Ile Ile
        120 *

AAG GAA TGC ACA CTC ACC AGC AAC ACC AAG TGC AAA GAG GAA GTG AAG AGA AAG GAA GTA CAG AAA
Lys Glu Cys Thr Leu Thr Ser Asn Thr Lys Cys Lys Glu Glu Val Lys Arg Lys Glu Val Gln Lys
    140                                 150                                         160

ACA TGC AGA AAG CAC AGA AAG GAA AAC CAA GGT TCT CAT GAA TCT CCA ACC TTA AAT CCT GAA ACA
Thr Cys Arg Lys His Arg Lys Glu Asn Gln Gly Ser His Glu Ser Pro Thr Leu Asn Pro Glu Thr
                                    170                                     180

GTG GCA ATA AAT TTA TCT GAT GTT GAC TTG AGT AAA TAT ATC ACT ACT ATT GCT GGA GTC ATG ACA
Val Ala Ile Asn Leu Ser Asp Val Asp Leu Ser Lys Tyr Ile Thr Thr Ile Ala Gly Val Met Thr
                            190                                 200

CTA AGT CAA GTT AAA GGC TTT GTT CGA AAG AAT GGT GTC AAT GAA GCC AAA ATA GAT GAG ATC AAG
Leu Ser Gln Val Lys Gly Phe Val Arg Lys Asn Gly Val Asn Glu Ala Lys Ile Asp Glu Ile Lys
                210                                             220
```

FIG. 3B

```
AAT GAC AAT GTC CAA GAC ACA GCA GAA CAG AAA GTT CAA CTG CTT CGT AAT TGG CAT CAA CTT CAT
Asn Asp Asn Val Gln Asp Thr Ala Glu Gln Lys Val Gln Leu Leu Arg Asn Trp His Gln Leu His
                230                                     240

GGA AAG AAA GAA GCG TAT GAC ACA TTG ATT AAA GAT CTC AAA AAA GCC AAT CTT TGT ACT CTT GCA
Gly Lys Lys Glu Ala Tyr Asp Thr Leu Ile Lys Asp Leu Lys Lys Ala Asn Leu Cys Thr Leu Ala
        250                                     260                                     270

GAG AAA ATT CAG ACT ATC ATC CTC AAG GAC ATT ACT AGT GAC TCA GAA AAT TCA AAC TTC AGA AAT
Glu Lys Ile Gln Thr Ile Ile Leu Lys Asp Ile Thr Ser Asp Ser Glu Asn Ser Asn Phe Arg Asn
                        280                                     290

GAA ATC CAA AGC TTG GTC TAG AGTGAAAAACAACAAATTCAGTTCTGAGTATATGCAATTAGTGTTGAAAAGATTCTTA
Glu Ile Gln Ser Leu Val End
                298

ATAGCTGGCTGTAAATACTGCTTGGTTTTTTACTGGGTACATTTTATCATTTATTAGGCTGAAGAGCCAACATATTTGTAGATTTTT

AATATCTCATGATTCTGCCTCCAAGGATGTGTTTAAAATCTAGTTGGGAAAACAAACTTCATCAAGAGTAAATGCAGTGGCATGCTAAGT

ACCCAAATAGGAGTGTATGCAGAGGATGAAAAGATTAAGATTATGCTCTGGCATCTAACATATGATTCTGTAGTATGAATGTAATCAGT

GTATGTTAGTACAAATGTCTATCCACAGGCTAACCCCACTCTATGAATCAATAGAAGAAGCTATGACCTTTTGCTGAAATATCAGTTA

CTGAACAGGCAGGCCACTTTGCCTCTAAATTACCTCTGATAATTCTAGAGATTTTACCATATTTCTAAACTTTGTTTATAACTCTGAG
```

FIG. 3C

AAGATCATATTTATGTAAAGTATATGTATTTGAGTGCAGAATTTAAATAAGGCTCTACCTCAAAGACCTTTGCACAGTTTATTGGTGT

CATATTATACAATATTTCAATTGTGAATTCACATAGAAAAACATTAAATTATATGTTTGACTATTATATATGTGTATGCATTTTACTG

GCTCAAAACTACCTACTTCTTTCTCAGGCATCAAAAGCATTTTGAGCAGGAGAGTATTACTAGAGCTTTGCCACCTCTCCATTTTTGC

CTTGGTGCTCATCTTAATGGCCTAATGCACCCCCAAACATGGAAATATCACCAAAAAATACTTAATAGTCCACCAAAAGGCAAGACTG

CCCTTAGAAATTCTAGCCTGGTTTGGGAGATACTAACTGCTCTCAGAGAAAGTAGCTTTGTGACATGTCATGAACCCATGTTTGCAATC

AAAGATGATAAAATAGATTCTTATTTTTCCCCCACCCCCGAAAATGTTCAATAATGTCCCATGTAAAACCTGCTACAAATGGCAGCTT

ATACATAGCAATGGTAAAATCATCATCTGGATTTAGGAATTGCTCTCTTGTCATACCCTCAAGTTTCTAAGATTTAAGATTCTCCTTACT

ACTATCCTACGTTTAAATATCTTTGAAAGTTTGTATTAAATGTGAATTTTAAGAAATAATATTTATATTTCTGTAAATGTAAACTGTG

AAGATAGTTATAAACTGAAGCAGATACCTGGAACCACCTAAAGAACTTCCATTTATGGAGGATTTTTTGCCCCTTGTGTTTGGAATT

ATAAAAATATAGGTAAAAGTACGTAATTAAATAATGTTTTG

FIG. 3D

EXTRACELLULAR: $^{44}$HLP CPP GER KAR D$^{56}$

TRANSMEMBRANE: $^{157}$NLG WLC LLL LPI PLI V$^{172}$

TRUNCATED (-TM): $^{147}$TKC KEE$^{152}$ $^{174}$VKR KEV$^{179}$

NUMBERED ACCORDING TO FULL LENGTH FAS POLYPEPTIDE SEQUENCE

FIG. 4

RECOMBINANT PRODUCTION OF A SOLUBLE SPLICE VARIANT OF THE FAS (APO-1) ANTIGEN, FAS TM

FIELD OF THE INVENTION

This invention relates generally to the field of apoptosis and specifically to a novel Fas protein.

BACKGROUND OF THE INVENTION

Apoptosis is a normal physiologic process that determines individual cell death and ultimate deletion of the cell from tissue. For review see, *Apoptosis the Molecular Basis of Cell Death*, Tomei and Cope, eds., Current Communications in Cell and Molecular Biology 3, Cold Spring Harbor Laboratory Press, New York, 1991. Apoptosis is a process of programmed cell death involved in a variety of normal and pathogenic biological events and can be induced by a number of unrelated stimuli. Changes in the biological regulation of apoptosis also occur during aging and are responsible for many of the conditions and diseases related to aging.

Recent studies of apoptosis have implied that a common metabolic pathway leading to cell death may be initiated by a wide variety of signals, including changes in hormone levels, serum growth factor deprivation, chemotherapeutic agents and ionizing radiation. Wyllie (1980) Nature, 284:555–556; Kanter et al. (1984) Biochem. Biophys. Res. Commun., 155:324–331; and Kruman et al. (1991) J. Cell. Physiol., 148:267–273. Agents that affect the biological control of apoptosis thus have therapeutic utility in a wide variety of conditions.

Fas, also known as APO-1, is a cell surface protein belonging to the tumor necrosis factor/nerve growth factor receptor family, each of whose members have been shown to be capable of mediating apoptosis. The cloning of Fas is described in PCT publication No. WO 91/10448; and European Patent Application Publication Number 0510691. Fas is a transmembrane (TM) protein of 34,971 deduced molecular weight and an apparent molecular weight of about 45,000 which may be due to glycosylation. The mature Fas molecule consists of 319 amino acid residues of which 157 are extracellular, 17 constitute the TM domain and 145 are intracellular. A variety of cell types express Fas on their surface. Interestingly, Fas expression is increased in activated T-cells including $CD4^+$ and $CD8^+$ cells.

Certain antibodies specific for Fas have been shown to induce death of cells that express Fas on their surfaces, by an apoptotic mechanism. Early studies indicated that therapeutic uses of antibodies specific to Fas would be effective in treating a variety of diseases. Itoh et al. (1991) Cell, 66:233–243; Krammer et al. (1991) in *Apoptosis: The Molecular Basis Of cell Death*, (Tomei and Cope, eds.), Cold Spring Harbor Laboratory Press, New York; Oehm et al. (1992) J. Biol. Chem., 267:10709–10715; and Rouvier et al. (1993) J. Exp. Med., 177:195–200. It has now been found that administration of anti-Fas antibodies can be lethal. Ogasawara et al. (1993) Nature 364:806–809. It has also been found that purified Fas blocks the cytocidal effects of anti-Fas. Oehm et al. (1992).

Increased levels of T cell surface Fas have also been associated with tumor cells and HIV-infected cells. HIV-infected cells are more sensitive to anti-Fas antibodies, yet the significance of the association of Fas with HIV infection has not yet been determined.

The endogenous Fas ligand, responsible for recognizing Fas and inducing apoptosis, has not been identified, although some AIDS patients have been shown to have increased levels of anti-Fas autoantibodies. Oehm et al. (1991). Moreover, T cell mediated cytotoxicity has been shown to be involved in Fas-mediated apoptosis.

All references cited herein both infra and supra are hereby incorporated herein by reference.

SUMMARY OF THE INVENTION

A novel native form of the Fas protein, (hereinafter, FasΔTM) lacking the transmembrane region is provided. DNA encoding FasΔTM and recombinant cells expressing the DNA are also provided. Diagnostic and therapeutic methods utilizing FasΔTM are also provided.

BRIEF DESCRIPTION OF THE DRAWINGS

FIG. 3A–D (SEQ ID NO. 18–19) depict the nucleotide and amino acid residue sequences of FasΔTM.

FIG. 4 (SEQ ID NO. 20–22) depicts synthetic peptides used to raise antibodies useful in the detection of biologically important Fas molecules. The peptides are numbered according to the full length Fas polypeptide sequence.

FIG. 5A depicts the results obtained with no anti-Fas and FIG. 5B depicts the results obtained in the presence of 5 ng/ml anti-Fas.

DETAILED DESCRIPTION OF THE INVENTION

The present invention is to an isolated novel, secreted form of Fas protein, hereinafter designated FasΔTM and methods of use of FasΔTM. The invention further includes the cloned DNA encoding FasΔTM and recombinant cells expressing the DNA. The nucleotide and amino acid residue sequences of FasΔTM are shown in FIG. 3A–D.

Figure 1:
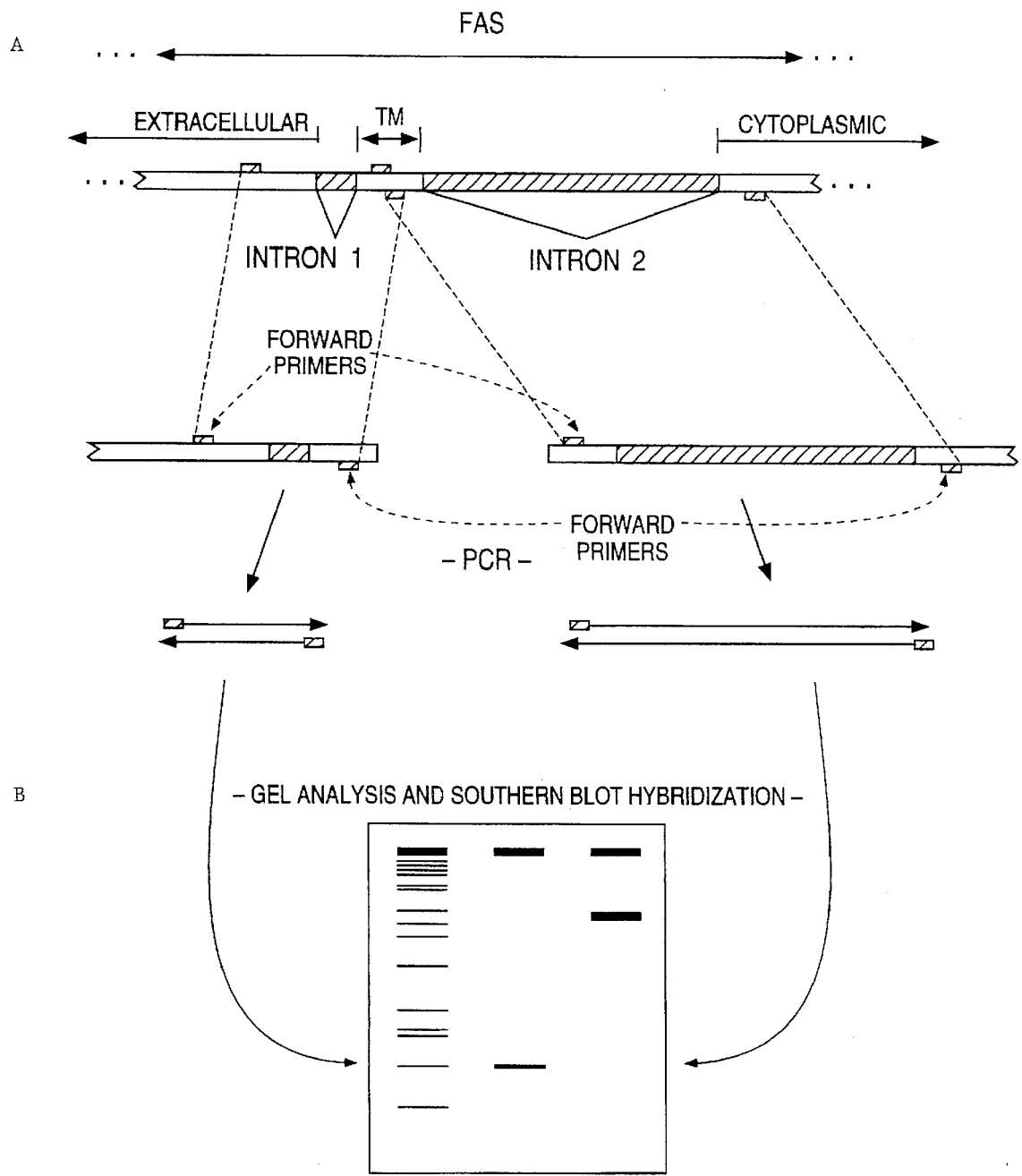
FIG. 1 is a schematic diagram depicting the Fas genomic DNA structure around the transmembrane region, (A) and the gel analysis and Southern blot hybridization pattern of the genes (B).

The genomic structure of the Fas gene, in the appropriate region, is depicted in FIG. 1A. The location of the introns and exons are related to the different regions of Fas. The cloning of FasΔTM is described in detail in the Examples below.

Figure 2:
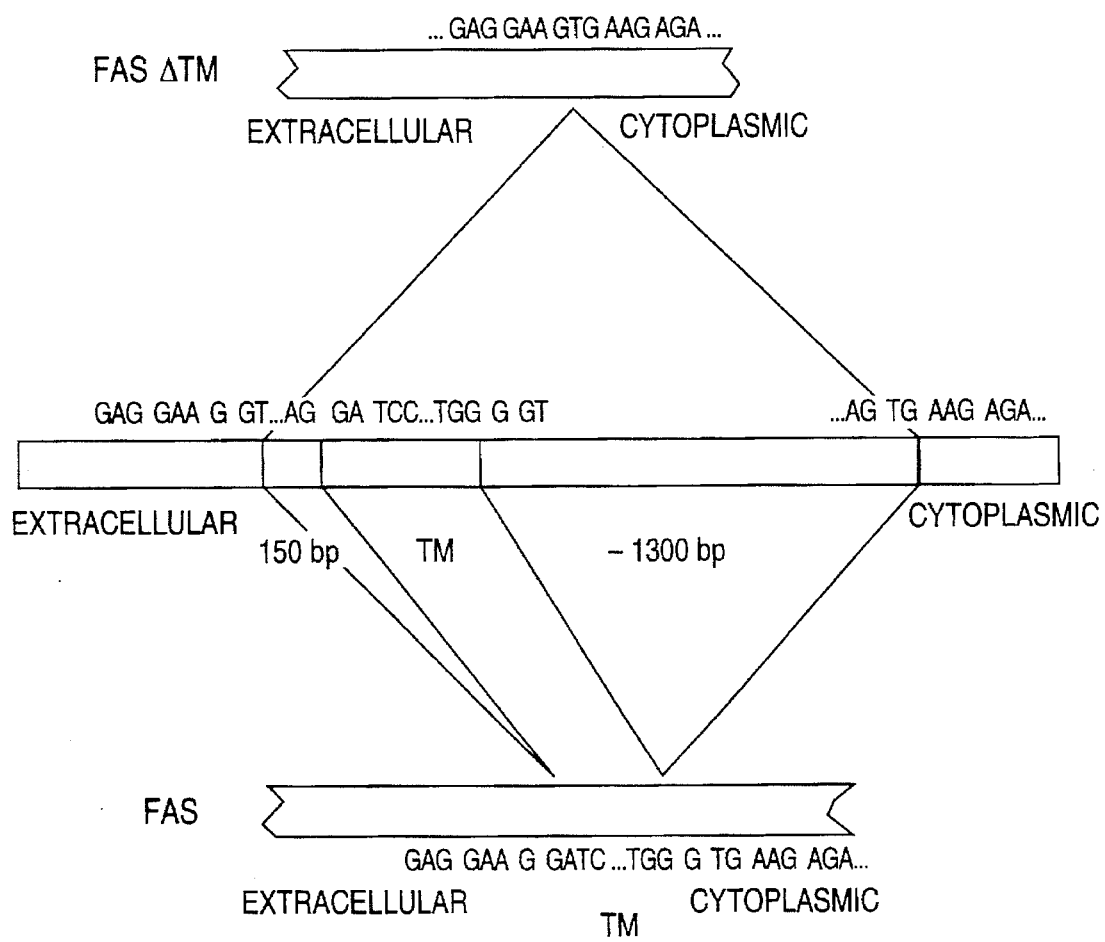
FIG. 2 (SEQ ID NO. 11–17) is a schematic diagram depicting alternate splicing of the Fas RNA to produce Fas and FasΔTM RNA.

FIG. 2 depicts the alternate splicing of the mRNA thought to result in the alternate forms of Fas however, the invention is not limited by the mechanism by which FasΔTM is produced. Native FasΔTM lacks twenty-one amino acid residues including the TM region.

The invention includes other recombinant variations of FasΔTM which lack a portion of the TM region sufficient to produce non-membrane bound protein. Preferably, the protein is secreted from the cell. The term FasΔTM encompasses all the non-membrane-bound forms of the molecule lacking TM region amino acid residues. FIG. 3 depicts the nucleotide and amino acid residue sequences of native FasΔTM.

One embodiment of the present invention is the DNA encoding FasΔTM. The DNA encoding FasΔTM includes, but is not limited to, the cDNA, genome-derived DNA and synthetic or semi-synthetic DNA. The nucleotide sequence of the cDNA encoding FasΔTM is shown in FIG. 3A–D. The DNA includes modifications such as deletions, substitutions and additions particularly in the noncoding regions. Such changes are useful to facilitate cloning and modify gene expression. Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems. Suitable conservative amino acid residue substitutions are known in the art and are discussed below.

Techniques for nucleic acid manipulation useful for the practice of the present invention are described in a variety of references, including but not limited to, *Molecular Cloning: A Laboratory Manual*, 2nd ed., Vol. 1–3, eds. Sambrook et al. Cold Spring Harbor Laboratory Press (1989); and *Current Protocols in Molecular Biology*, eds. Ausubel et al., Greene Publishing and Wiley-Interscience: New York (1987) and periodic updates.

The invention further embodies a variety of DNA vectors having cloned therein the nucleotide sequence encoding FasΔTM. Suitable vectors include any known in the art including, but not limited to, those for use in bacterial, mammalian and insect expression systems. Specific vectors are known in the art and need not be described in detail herein. The vectors may also provide inducible promoters for expression of FasΔTM. Inducible promoters are those which do not allow constitutive expression of the gene but rather, permit expression only under certain circumstances. Such promoters may be induced by a variety of stimuli including, but not limited to, exposure of a cell containing the vector to a ligand, chemical or change in temperature.

These promoters may also be cell-specific, that is, inducible only in a particular cell type and often only during a specific period of time. The promoter may further be cell cycle specific, that is, induced or inducible only during a particular stage in the cell cycle. The promoter may be both cell type specific and cell cycle specific. Any inducible promoter known in the art is suitable for use in the present invention.

The invention further includes a variety of expression systems transfected with the vectors. Suitable expression systems include but are not limited to bacterial, mammalian and insect. Specific expression systems are known in the art and need not be described in detail herein. It has been found that the baculovirus expression system described below provides expression of biologically active FasΔTM. For expressing FasΔTM for therapeutic purposes however, mammalian expression systems, such as Chinese hamster ovary (CHO) cells, may be preferred to ensure proper post-translational modification.

The invention encompasses cells removed from animals, including man, transfected with vectors encoding FasΔTM and reintroduced into the animal. Suitable transfected cells also include those removed from a patient, transfected and reintroduced into the patient. Any cells can be treated in this manner. Suitable cells include, but are not limited to, cardiomyocytes and lymphocytes. For instance, lymphocytes, removed, transfected with the recombinant DNA and reintroduced into an HIV-positive patient may increase the half-life of the reintroduced T cells.

Preferably, for treatment of HIV-infected patients, the white blood cells are removed and sorted to yield the $CD4^+$ cells. The $CD4^+$ cells are then transfected with a vector encoding FasΔTM and reintroduced into the patient. Alternatively, the unsorted lymphocytes can be transfected with a recombinant vector encoding the FasΔTM gene under the control of a cell-specific promoter such that only $CD4^+$ cells express the FasΔTM gene. In this case, an ideal promoter would be the CD4 promoter, however, any suitable $CD4^+$ T cell-specific promoter can be used.

Further, the invention encompasses cells transfected in vivo by the vectors. Suitable methods of in vivo transfection are known in the art and include, but are not limited to, that described by Zhu et al. (1993) Science 261:209–211. In the case of in vivo transfection, it is preferred that the transfection is cell-type specific or that the promoter is cell-specific.

Transgenic animals containing the recombinant DNA vectors are also encompassed by the invention. Methods of making transgenic animals are known in the art and need not be described in detail herein. For a review of methods used to make transgenic animals, see PCT publication no. WO 93/04169. Preferably, such animals express a recombinant FasΔTM gene under control of a cell-specific and, even more preferably, a cell cycle specific promoter.

Purification or isolation of FasΔTM expressed either by the recombinant DNA or from biological sources such as sera can be accomplished by any method known in the art. Since native and most recombinant FasΔTM is secreted from the cells, purification is simplified by the fact that it appears in the supernatant of in vitro cultures and in sera in vivo and no cell disruption is required as is the case with Fas. Protein purification methods are known in the art. Generally, substantially purified proteins are those which are free of other, contaminating cellular substances, particularly proteins. Preferably, FasΔTM is more than eighty percent pure and most preferably FasΔTM is more than ninety-five percent pure. For clinical use as described below, FasΔTM is preferably highly purified, at least about ninety-nine percent pure, free of pyrogens and other contaminants.

Suitable methods of purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention also includes the substantially purified FasΔTM protein having the amino acid residue sequence depicted in FIG. 3A–D, and any protein lacking a sufficient portion of the TM region to be secreted from the cell. The invention encompasses functionally equivalent variants of FasΔTM which do not significantly affect its properties. For instance, conservative substitutions of amino acid residues, one or a few amino acid deletions or additions, and substitution of amino acid residues by amino acid analogs are within the scope of the invention.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of FasΔTM is encompassed by the present invention.

mRNA encoding FasΔTM has been detected in a variety of human organs and tissues. These include liver; heart;

peripheral blood lymphocytes (PBLs), both activated and normal; placenta; fibroblasts, both normal and phorbol ester treated and SV40 infected; and several cell lines including U937, WIL-2 and IM9. FasΔTM has also been found to be secreted from the cell rather than remain membrane-bound, even though it retains the cytoplasmic region of the membrane-bound form of the protein. FasΔTM can thus be detected in sera as a soluble protein. Any antibody that recognizes Fas is suitable for use in recognizing FasΔTM.

In another embodiment, diagnostic methods are provided to detect the expression of FasΔTM either at the protein level or the mRNA level. The soluble FasΔTM protein is likely to be found in the sera of patients with diseases associated with apoptosis defects, and is therefore useful as a diagnostic tool for detecting and monitoring biological conditions associated with such apoptosis defects.

FasΔTM can be detected by any antibody, either polyclonal or monoclonal, that recognizes Fas. The distinction between Fas and FasΔTM can be determined by the solubility of the protein. Fas is membrane bound and can thus be removed from soluble proteins by removal of cells and/or membranes. FasΔTM remains soluble. Alternatively, antibodies specific for FasΔTM and not Fas are encompassed by the present invention. Such antibodies can be generated by using FasΔTM as the antigen or, preferably, peptides encompassing the region in FasΔTM that differs from Fas, the TM region. Examples of such peptides are depicted in FIG. 4. Methods of detecting proteins using antibodies and of generating antibodies using proteins or synthetic peptides are known in the art and need not be described in detail herein.

FasΔTM protein expression can also be monitored by measuring the level of mRNA encoding FasΔTM. Any method for detecting specific mRNA species is suitable for use in this method. This is easily accomplished using the polymerase chain reaction (PCR). Preferably, the primers chosen for PCR flank the TM region so as to provide a product that is measurably distinct in size between Fas and FasΔTM. Alternatively, Northern blots can be utilized to detect the specific mRNA species either by size or by probes specific to the mRNA encoding the TM region.

The invention also encompasses therapeutic methods and compositions involving treatment with FasΔTM. Either native or recombinant FasΔTM is suitable for use in this composition. Both should be substantially pure and free of pyrogens. It is preferred that the recombinant FasΔTM be produced in a mammalian cell line so as to ensure proper glycosylation. FasΔTM may also be produced in an insect cell line and will be glycosylated.

For therapeutic compositions, a therapeutically effective amount of substantially pure FasΔTM is suspended in a physiologically accepted buffer including, but not limited to, saline and phosphate buffered saline (PBS) and administered to the patient. Preferably administration is intravenous. Other methods of administration include but are not limited to, subcutaneous, intraperitoneal, gastrointestinal and directly to a specific organ, such as intracardiac, for instance, to treat cell death related to myocardial infarction.

Suitable buffers and methods of administration are known in the art. The effective concentration of FasΔTM will need to be determined empirically and will depend on the type and severity of the disease, disease progression and health of the patient. Such determinations are within the skill of one in the art. Moreover, FasΔTM is a human protein normally found in the sera; administration of exogenous human FasΔTM is not likely to induce reactions such as anaphylactic shock or the production of antibodies. The upper concentration of FasΔTM for therapeutic use is thus not limited by these physiological considerations.

Administration of FasΔTM results in an increased extracellular concentration of FasΔTM which competitively binds the Fas ligand and therefore prevents or ameliorates apoptotic signals transmitted by Fas to the cell. The therapeutic method thus includes, but is not limited to, inhibiting Fas-mediated cell death. For instance, tumor necrosis factor (TNF) and Fas-specific antibodies are known to induce apoptosis and even whole animal death by binding to Fas. Inhibition of this interaction of Fas and ligands which induce it to trigger apoptosis thus will reduce apoptosis.

Suitable indications for therapeutic use of FasΔTM are those involving Fas-mediated cell death and include, but are not limited to, conditions in which there is inappropriate expression or up-regulation of Fas or the Fas ligand. Such indications include but are not limited to HIV infection, autoimmune diseases, cardiomyopathies, neuronal disorders, hepatitis and other liver diseases, osteoporosis, and shock syndromes, including, but not limited to, septicemia.

Methods of treatment with FasΔTM also include other mechanisms of increasing the extracellular concentration of FasΔTM. These include, but are not limited to, increasing cellular expression of FasΔTM. Suitable methods of increasing cellular expression of FasΔTM include, but are not limited to, increasing endogenous expression and transfecting the cells with vectors encoding FasΔTM. Cellular transfection is discussed above and is known in the art. Increasing endogenous expression of FasΔTM can be accomplished by exposing the cells to biological modifiers that directly or indirectly increase levels of FasΔTM either by increasing expression or differential processing of the FasΔTM over Fas or by decreasing FasΔTM degradation. Suitable biological modifiers can be determined by exposing cells expressing FasΔTM under the control of the native Fas promoter to potential biological modifiers and monitoring expression of FasΔTM. Expression of FasΔTM can be monitored as described above either by protein or mRNA levels. Biological modifiers can be any therapeutic agent or chemical known in the art. Preferably, suitable biological modifiers are those lacking substantial cytotoxicity and carcinogenicity.

Likewise, biological modifiers which reduce endogenous levels of FasΔTM are encompassed by the invention as is a method of increasing Fas-mediated cell death by decreasing endogenous levels of FasΔTM. The method of determining suitable biological modifiers is as discussed above, except that the endpoint is decreased levels of FasΔTM. Other methods of decreasing endogenous levels of FasΔTM include, but are not limited to, antisense nucleotide therapy and exposure to anti-FasΔTM antibody. Both these methods are known in the art and their application will be apparent to one of skill in the art. Suitable indications for decreasing endogenous levels of FasΔTM will be any which Fas-mediated cell death is appropriate. These include, but are not limited to, various types of malignancies and other disorders resulting in uncontrolled cell growth such as eczema.

The following examples are provided to illustrate but not limit the present invention.

EXAMPLE 1

Cloning of FasΔTM

Nucleic acid sequences encoding FasΔTM were cloned as follows. Unless otherwise specified, all cloning techniques were essentially as described by Sambrook et al. (1989) and all reagents were used according to the manufacturer's instructions.

mRNA was obtained from human lymphocytes and PCR was used to make cDNA specific for the FasΔTM mRNA. The lymphocytes were obtained and processed as follows. 35 ml of blood was obtained by venipuncture from a normal 42 year old male and immediately added to 350 μl 15% EDTA. 35 ml PBS was added to the blood and 17 ml of the blood suspension was layered on 12.5 ml Ficoll Paque (Pharmacia). This was then centrifuged at 1,800 rpm for 30 minutes in a swinging bucket rotor and a DynacII centrifuge.

The plasma was aspirated and the lymphocyte layer collected and added to two volumes of PBS containing 0.9 mM $Ca^{2+}$ and 0.5 mM $Mg^{2+}$ (PBS/Ca/Mg buffer). The cells were washed once with the PBS/Ca/Mg buffer and resuspended in RPMI (Gibco/BRL) medium containing 2 g/l glucose and 10% fetal bovine serum (FBS) at $2\times10^6$ cells/ml. The cell yield was $3.5\times10^7$ with greater than 98% viability. Concanavalin A (Sigma) was added to a final concentration of 30 μg/ml and the cells were incubated at 37° C. for 72 hr.

The cells were then processed for RNA isolation as follows. Total RNA was isolated from $3\times10^6$ cells using the guanidinium thiocyanate single-step RNA isolation method according to "Current Protocols in Molecular Biology" (1991). The first strand cDNA used in the PCR reaction was synthesized from 6.4 μg of total RNA and resuspended in 100 μl water, according to the method described by Zapf et al. (1990) J. Biol. Chem., 265:14892–14898. The FasΔTM cDNA was synthesized using PCR. The forward primer: 5'-GATTGCTTCTAGACCAT-GCTGGGCATCTGGACCCTCCTACC-3'(SEQ ID NO:1) contained an XbaI restriction site, and encoded the initiation methionine codon and first eight codons of Fas.

The reverse primer: 5'-GTTGTTTGTCGACCTAGAC-CAAGCTTTGGATTTCATTTCTG-3'(SEQ ID NO:2) contained SalI restriction site, and encoded the termination codon and last eight codons of Fas.

The PCR reaction was performed by adding to 1 μl of template cDNA (as-described above, diluted 1:100), 100 pmoles of each primer, 2.5 units Amplitaq, 76.5 μl $H_2O$ and 10 μl buffer. The reaction proceeded at 94° C. for 1 min, 55° C. for 2 min, 72° C. for 3 min for 35 cycles, 72° C. for 7 min and was stored at 4° C. 15 μl of the reaction mix was loaded on a 1% agarose gel and a band of the appropriate molecular weight was detected. The remaining reaction mix was extracted with phenol/chloroform, ethanol precipitated and resuspended in 80 μl Tris-EDTA (TE).

To the 80 μl sample the following was added: 5 μl SalI; 5 μl XbaI; 10 μl SalI reaction buffer. In another reaction, 60 μl $H_2O$ was added to 20 μl pBluescript at 0.65 mg/ml, 5 μl SalI, 5 μl XbaI and 10 μl SalI reaction buffer. Both tubes were incubated at 37° C. for 2 hours and the reactions were run on a 1% preparative agarose gel. Bands corresponding to the digested DNA were excised from the gel and purified by Elutip® according to the manufacturer's instructions. The purified FasΔTM cDNA was resuspended in 20 μl TE buffer and the pBluescript in 40 μl TE buffer.

The DNA samples were ligated in a reaction mixture containing 2 μl vector, 8 μl FasΔTM cDNA, 2 μl μ10 mM ATP, 2 μl 10×ligation buffer, 2 μl T4 DNA ligase (New England Biolabs) and 4 μl $H_2O$. The control reaction contained no FasΔTM DNA. After allowing the ligation to continue for 6 hr at 14° C. the DNA was used to transform DH5α cells (Gibco) according to the manufacturer's instructions. Briefly, 200 μl cells were added to the ligation mix and kept on ice for 45 min. The cells were heat shocked for 90 sec at 42° C. and then placed on ice. 3 ml L broth was then added and the cells were incubated for 1 hr at 37° C and plated on L broth agar plates containing 100 mM ampicillin, 20 μl 4% X-Gal and 50 μl 100 mM isopropyl-1-β-D-thiogalactoside (IPTG). The cells were allowed to form colonies by incubating overnight at 37° C. Positive colonies were grown overnight in L broth plus ampicillin, the plasmids were obtained by an alkaline lysis procedure and digested with SalI and XbaI according to the manufacturer's instructions. One plasmid containing the appropriate insert was prepared on a large-scale and the insert was sequenced by the dideoxy method. The sequence obtained is presented in FIG. 3A–D. The plasmid containing the recombinant cDNA encoding FasΔTM was designated pBluescript-FasΔTM.

EXAMPLE 2

Analysis of Fas Genomic Structure

The intron-exon organization in the Fas TM region was determined by PCR. Primers were designed to flank each of the putative introns, 1 and 2 (see FIG. 2). The forward and reverse primers flanking intron 1 were 5'-GATTGCTTCTAGAGGAATCA TCAAGGAATGCACACTC-3'(SEQ ID NO:3) and 5'-GTTGTTTGTCGACC CAAACAATTAGTGGAATTGGCAA-3'(SER ID NO:4) respectively, and the forward and reverse primers for intron 2 were 5'-AGATCTGCGGCCGCAT TGGGGTGGCTTTGTCTTCTT-3'(SEQ ID NO:5) and 5'-GTTGTTTGTCGACGTTTTCCT TTCTGTGCTTCTGCA-3'(SEQ ID NO:6) 5 respectively. XbaI and SalI restriction enzyme sites and NotI and SalI restriction enzyme sites were included at the 5' ends of the intron 1 and 2 primers respectively to facilitate cloning of the PCR products. PCR was performed according to the manufacturer's instructions (Perkin Elmer Cetus) using human genomic DNA (Clontech) (5 μg) as template. 30 cycles of PCR were performed in a Perkin Elmer Cetus DNA Thermal Cycler with each cycle consisting of a 94° C., 1 min denaturation step, a 55° C., 2 min annealing step, and a 72° C., 3 min extension step. An additional 7 minute extension step was included after the last cycle. The PCR products were then incubated with 5 units of DNA polymerase I, Klenow fragment at 37° C., 30 min, extracted with phenol/chloroform/isoamylalcohol (1:1:0.04) followed by chloroform/isoamylalcohol (24:1) and recovered by ethanol precipitation.

The intron 1 and intron 2 PCR products were digested with XbaI and SalI and NotI and SalI respectively, agarose gel purified, ligated into pBluescript SK(–) and introduced into E. coli strain HB101 by the methods described in Example 1. Plasmid DNA was isolated using a Promega Magic miniprep kit according to the method described by the manufacturer. Plasmid DNA was sequenced directly by the dideoxy chain termination method using the Sequenase Version 2.0 DNA Sequencing kit according to the manufacturer's instructions (USB). The sequence obtained is depicted in FIG. 3A–D.

EXAMPLE 3

Expression of Recombinant FasΔTM

In order to express recombinant FasΔTM in the baculovirus system, the plasmid obtained in Example 1 was used to generate a second FasΔTM vector, designated pBlueBacIII- FasΔTM, by a PCR methodology as described in Example 1. The forward primer, 5'-TTTCCCGGATCCACAACCATGCTGGGCATCTGG ACCCTCCTA-3'(SEQ ID NO:7) contained the convenient BamHI restriction site, and a Kozak consensus sequence ACAACC immediately preceding the initiation codon, and encoded the first seven amino acids of Fas. The reverse primer 5'-CCCCATGGCTAGACCAAGCTTTG GATTTCATT-3'(SEQ ID NO:8) encoded a termination codon, a NcoI site, and the last seven amino acids of Fas. Five recombinant plasmids were isolated. Two of them were sequenced by the dideoxy terminator method (Sanger et al., 1977) using sequencing kits according to the manufacturer's instructions (USB, Sequenase version 2.0). The DNA was sequenced using internal primers.

Clone 3, which did not contain any PCR errors in the sequence, was used to generate recombinant viruses by in vivo homologous recombination between the overlapping sequences pBlueBac III-FasΔTM-3 and AcNPV wild type baculovirus. After 48 hours post-transfection in insect Spodoptera frugiperda clone 9 (SF9) cells, the recombinant viruses were collected, identified by PCR and further purified. Standard protocols for plasmid cloning were employed (Maniatis et al., 1982). Standard procedures for selection, screening and propagation of recombinant baculovirus were performed according to the manufacturer's instructions (Invitrogen). After 48 hours post-transfection, the recombinant viruses were collected and purified. The molecular mass, on sodium dodecyl sulfate-polyacrylamide gel electrophoresis (SDS-PAGE), of the protein produced in the baculovirus system is identical to the predicted molecular mass of FasΔTM according to the amino-acid sequence and the recombinant protein was also recognized by an anti-Fas antibody (Medical and Biological Laboratories, Nagoya, Japan).

EXAMPLE 4

Expression of FasΔTM in Mammalian Systems

The FasΔTM coding sequence was excised from pBluescript-FasΔTM with XbaI and SalI, and introduced into plasmids pCEP7 and pREP7 (Invitrogen) at compatible NheI and XhoI sites to generate clones FasΔTM-1 and FasΔTM-7, respectively. pCEP7 was generated by removing the RSV 3'-LTR of pREP7 with XbaI/Asp718, and substituting the CMV promoter from pCEP4 (Invitrogen). To generate a compatible XbaI site, pCEP4 was first cleaved with SalI, and ligated to an oligonucleotide adapter containing an external SalI site, and an internal NheI site. pCEP4 was then cleaved with NheI and Asp718 and the purified CMV promoter was ligated into pREP7 to generate pCEP7. 25 μg of each FasΔTM-containing plasmid was electroporated into the B lymphoblastoid cell line WIL-2, and stable hygromycin resistant transformants were selected.

EXAMPLE 5

Anti-Fas Antibody Induced Death of the Wild Type B Lymphoblastoid Cell Line WI-L2-729 HF2 and the Wild Type Cell Transformed by FasΔTM-1 and FasΔTM-7

Figure 5A:
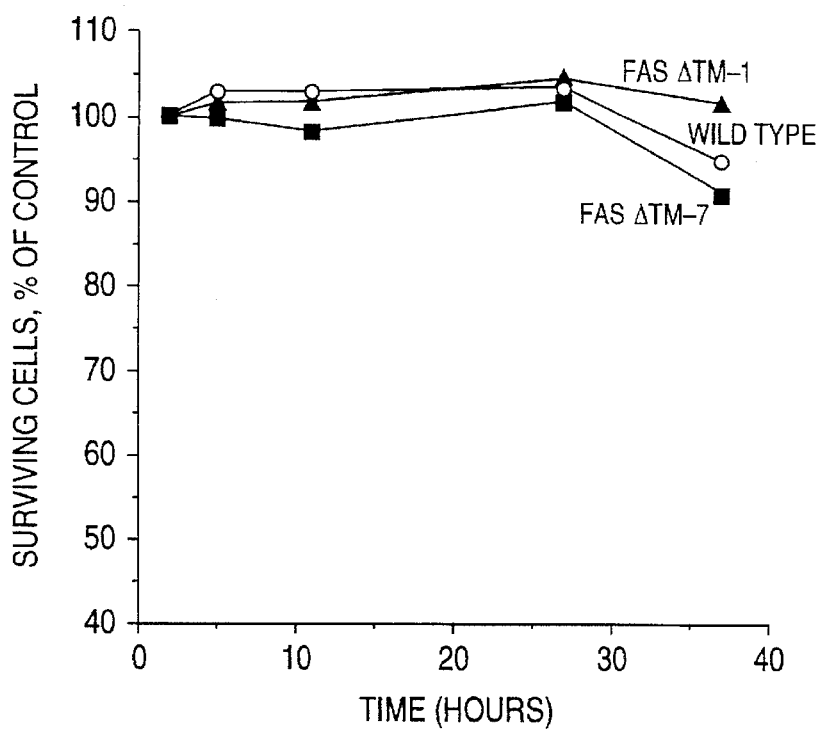
FIG. 5A and B depict anti-Fas induced death of WIL-2 cells transformed with FasΔTM.
Figure 5B:
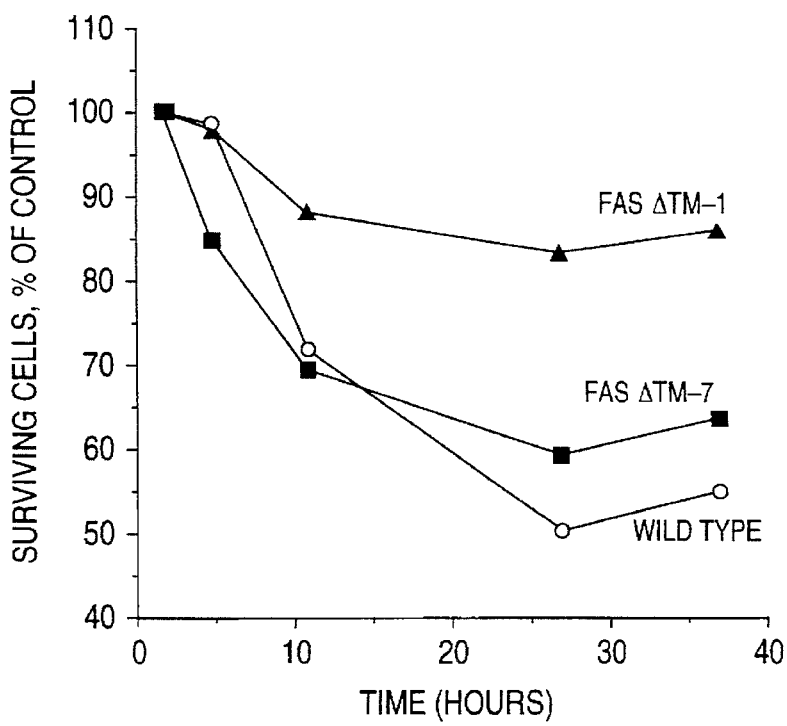

$2\times10^5$ WIL-2, FasΔTM-1 and FasΔTM-7 transformed WIL-2 cells were grown in RPMI supplemented with 10% fetal bovine serum (FBS). After washing with fresh medium, the cells were suspended in RPMI supplemented with 10% FBS, 50 ng anti-Fas antibody was added, and the kinetics of cell death were analyzed by flow cytometry with FACScan. This method is based on the measurement of cells which shrink and are permeable to propidium iodide (PI) following their death. There was no difference in survival of all three cell lines in the control, but upon addition of anti-Fas antibodies, cells transformed by FasΔTM were less sensitive: by 26 hrs treatment approximately 50%, 40%, and 16% of wild type WIL-2, FasΔTM-7, and FasΔTM-1 transformants died respectively (FIG. 5A and B).

Figure 6:
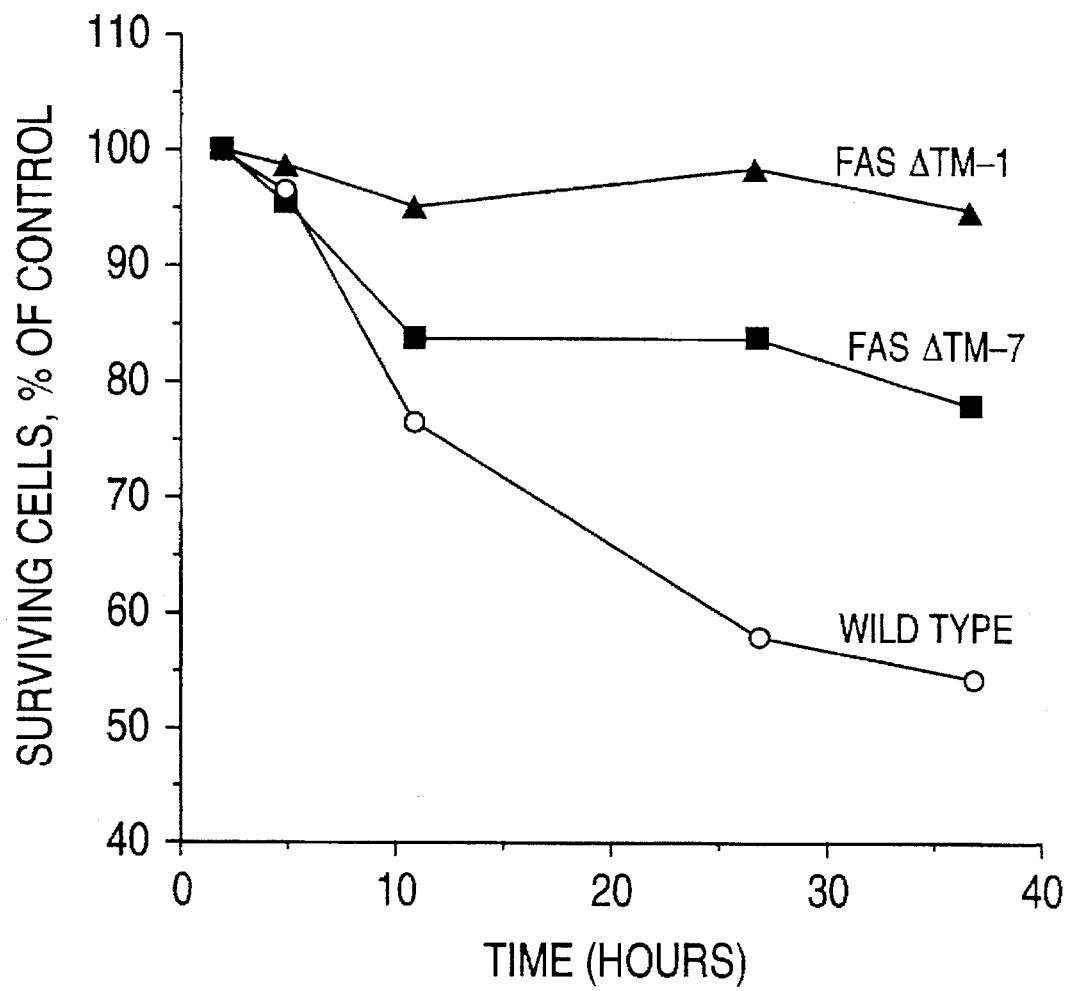
FIG. 6 depicts the anti-Fas induced death of WIL-2 cells transformed with FasΔTM (anti-Fas was added 24 hours after seeding).

In another series of experiments, cells were initially grown for 24 hrs and then anti-Fas antibodies were added under the assumption that FasΔTM was secreted and should accumulate in medium. In this case the sensitivity of transformed cell lines was lower then without preincubation: after 26 hrs treatment with antibodies about 45%, 16%, and 5% of wild type WIL-2, FasΔTM-7, and FasΔTM-1 transformants died respectively (FIG. 6).

Figure 7:
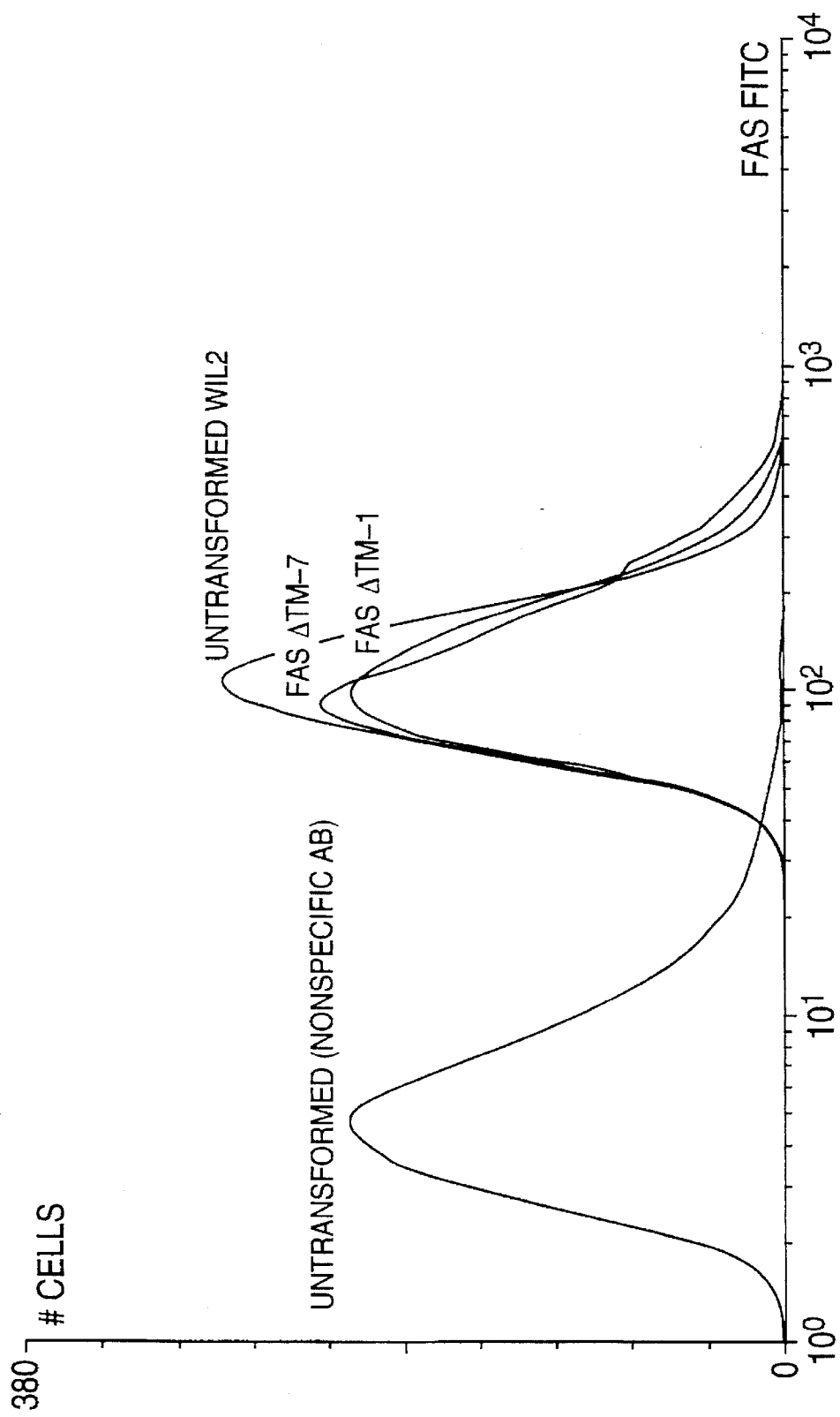
FIG. 7 depicts WIL-2/FasΔTM transformants: cell surface Fas.

To ensure that lower sensitivity of transformants is not caused by down regulation of Fas expression the amount of Fas on the surface of all three cell lines was compared. The cells were treated by standard procedures with monoclonal mouse anti-Fas antibodies, biotin-labeled anti-mouse IgM antibodies, and finally stained with FITC-labeled streptavidin. Analysis of stained cells using FACScan showed that there were no differences in the amount of Fas on the surface of wild type WIL-2 and the transformants (FIG. 7). Thus WIL-2 transformed with FasΔTM are less sensitive to the cytotoxic effect of anti-Fas antibodies. This effect may be explained at least in part by secretion of FasΔTM by transformants. Thus, increased cellular expression of FasΔTM results in inhibition of Fas-mediated cell death.

EXAMPLE 6

Recombinant FasΔTM Prevents Cell Death Induced by Anti-Fas Antibodies

Figure 8:
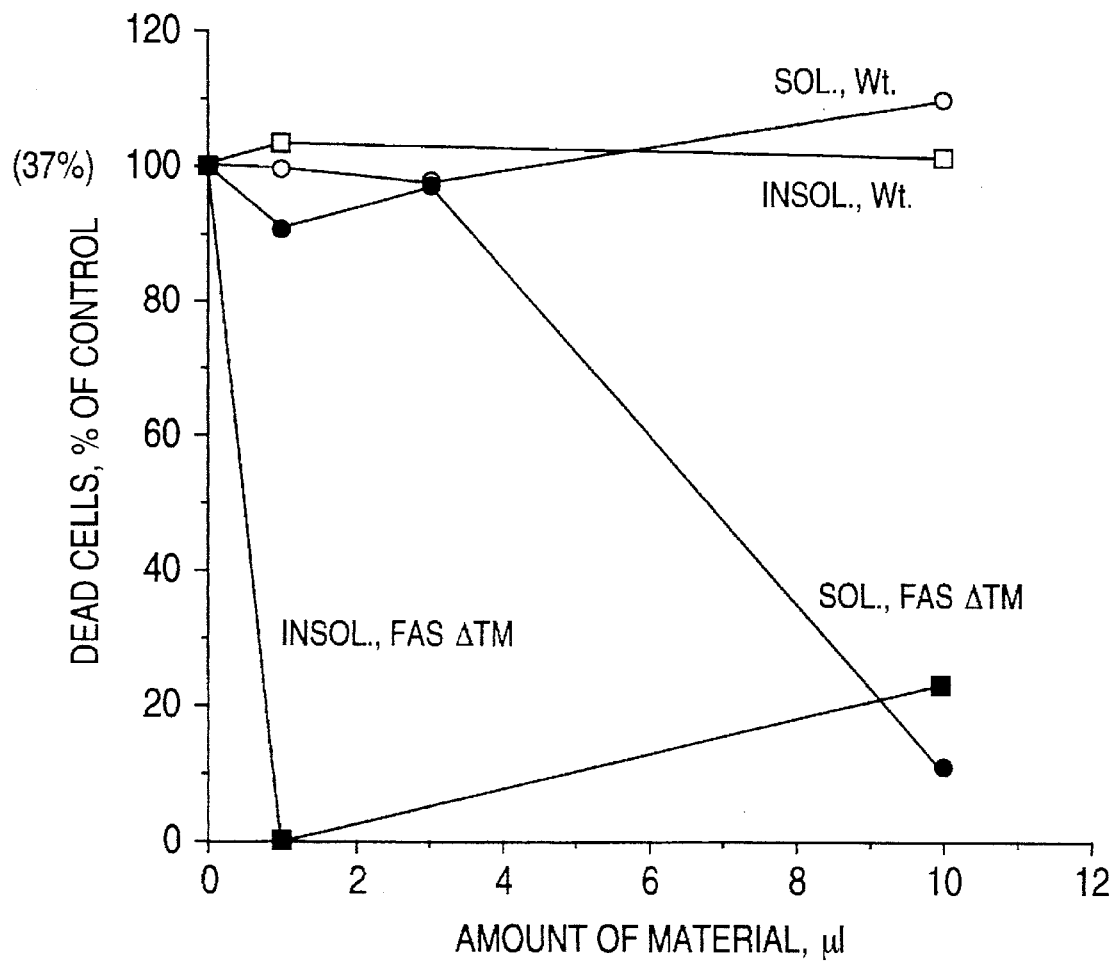
FIG. 8 depicts data showing that baculovirus-FasΔTM preparations prevent anti-Fas induced death of WIL-2 cells.

To check the biological activity of FasΔTM produced in a baculovirus system, insect cells transfected with wild type baculovirus and recombinant containing FasΔTM, as described in Example 3, were homogenized in water or in buffer containing 0.05% nonionic detergent Triton X-100 and centrifuged. Anti-Fas antibodies were preincubated 2 hrs at room temperature with aliquots of soluble and insoluble fractions, added to WIL-2, and cell death was analyzed after 24 hrs by flow cytometry as described above. There was no effect on cell viability of both soluble and insoluble fractions from insect cells transfected with the wild type baculovirus. At the same time soluble and insoluble fractions from insect cells transfected with baculovirus recombinant containing FasΔTM inhibited death of WIL-2 induced by anti-Fas antibodies. Activity of the insoluble fraction was approximately ten times higher than that of the soluble fraction (FIG. 8). Thus, recombinant FasΔTM can compete with Fas on the cell surface for binding antibodies and preventing Fas-mediated cell death.

EXAMPLE 7

FasΔTM transcript analysis by RT-PCR

Native FasΔTM transcripts were identified by RT-PCR and acrylamide gel electrophoresis. PCR primers were designed around the Fas TM region so that the Fas and FasΔTM transcripts would yield 296 bp and 233 bp PCR products, respectively. The forward primer was 5'-GACCCAGAATACCAAGTGCAGATGTA-3'(SEQ ID NO:9) and the reverse primer was 5'-CTGTTTCAGGATTTAAGGTTGGAGATT-3'(SEQ ID NO:10). cDNA was synthesized from poly(A)+ or total RNA isolated from various human tissues and cell lines. These included heart, liver, activated and non-activated peripheral blood lymphocytes (PBLs), placenta and fibroblast cell lines. PCR was performed as described in Example 1 using the cDNA as templates (10–100 ng/ml) and products were analyzed on 7% acrylamide/TBE gels.

All tissues and cell lines tested contained Fas and FasΔTM transcripts by this analysis. This suggests that cell death in these tissues can be modulated by the amounts (and ratios) of Fas and FasΔTM. Interestingly, liver contained the largest amounts of FasΔTM transcripts suggesting FasΔTM may be secreted into serum.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. A purified nucleic acid comprising a contiguous nucleotide sequence encoding a FasΔTM polypeptide which has an amino acid sequence corresponding to the sequence of a human Fas antigen which is capable of signaling in response to a ligand therefor, wherein the FasΔTM polypeptide comprises the intracellular and extracellular domains of said Fas antigen but lacks a portion of the transmembrane domain of said Fas antigen sufficient to produce a soluble, secreted protein upon the translation of said nucleic acid in a suitable mammalian host cell.

2. The nucleic acid according to claim 1, wherein the nucleic acid is cDNA.

3. The nucleic acid according to claim 1, encoding the FasΔTM amino acid sequence shown in SEQ ID NO:19.

4. The nucleic acid according to claim 1, having the nucleotide sequence depicted in SEQ ID NO:18.

5. A recombinant DNA vector comprising the nucleic acid according to claim 1.

6. The recombinant DNA vector according to claim 5 wherein expression of the nucleic acid encoding FasΔTM is under control of an inducible promoter.

7. The recombinant DNA vector according to claim 5 selected from the group consisting of pBlueBACIII™-FasΔTM-3, pBluescript™-FasΔTM, FasΔTM-1 and FasΔTM-7.

8. A cultured cell transfected with the recombinant DNA vector according to claim 5.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GATTGCTTCT AGACCATGCT GGGCATCTGG ACCCTCCTAC C    41

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTTGTTTGTC GACCTAGACC AAGCTTTGGA TTTCATTTCT G    41

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATTGCTTCT AGAGGAATCA TCAAGGAATG CACACTC    37

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTTGTTTGTC GACCCAAACA ATTAGTGGAA TTGGCAA    37

( 2 ) INFORMATION FOR SEQ ID NO:5:

( i ) SEQUENCE CHARACTERISTICS:
        ( A ) LENGTH: 39 base pairs
        ( B ) TYPE: nucleic acid (C) STRANDEDNESS: single
            (D) TOPOLOGY: linear (xi) SEQUENCE DESCRIPTION: SEQ ID NO:5:

AGATCTGCGG CCGCATTGGG GTGGCTTTGT CTTCTTCTT                        39

(2) INFORMATION FOR SEQ ID NO:6:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:6:

GTTGTTTGTC GACGTTTTCC TTTCTGTGCT TTCTGCA                          37

(2) INFORMATION FOR SEQ ID NO:7:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:7:

TTTCCCGGAT CCACAACCAT GCTGGGCATC TGGACCCTCC TA                    42

(2) INFORMATION FOR SEQ ID NO:8:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:8:

CCCCATGGCT AGACCAAGCT TTGGATTTCA TT                               32

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:9:

GACCCAGAAT ACCAAGTGCA GATGTA                                      26

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:10:

CTGTTTCAGG ATTTAAGGTT GGAGATT                                     27

(2) INFORMATION FOR SEQ ID NO:11:

(i) SEQUENCE CHARACTERISTICS:
            (A) LENGTH: 15 base pairs
            (B) TYPE: nucleic acid
            (C) STRANDEDNESS: single
            (D) TOPOLOGY: linear ( x i ) SEQUENCE DESCRIPTION: SEQ ID NO:11:

GAGGAAGTGA AGAGA                                                                 15

( 2 ) INFORMATION FOR SEQ ID NO:12:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GAGGAAGGT                                                                         9

( 2 ) INFORMATION FOR SEQ ID NO:13:

( i ) SEQUENCE CHARACTERISTICS:
    ( A ) LENGTH: 7 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

AGGATCC                                                                           7

( 2 ) INFORMATION FOR SEQ ID NO:14:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

TGGGGT                                                                            6

( 2 ) INFORMATION FOR SEQ ID NO:15:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

AGTGAAGAGA                                                                       10

( 2 ) INFORMATION FOR SEQ ID NO:16:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

GAGGAAGGAT C                                                                     11

( 2 ) INFORMATION FOR SEQ ID NO:17:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

TGGGTGAAGA GA                                                                         12

( 2 ) INFORMATION FOR SEQ ID NO:18:

( i ) SEQUENCE CHARACTERISTICS:
    ( A ) LENGTH: 2471 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 195..1136

( i x ) FEATURE:
    ( A ) NAME/KEY: mat_hd —peptide
    ( B ) LOCATION: 243

( x i ) SEQUENCE DESCRIPTION: SEQ ID NO:18:

```
GACGCTTCTG GGGAGTGAGG GAAGCGGTTT ACGAGTGACT TGGCTGGAGC CTCAGGGGCG        60

GGCACTGGCA CGGAACACAC CCTGAGGCCA GCCCTGGCTG CCCAGGCGGA GCTGCCTCTT       120

CTCCCGCGGG TTGGTGGACC CGCTCAGTAC GGAGTTGGGG AAGCTCTTTC ACTTCGGAGG       180

ATTGCTCAAC AACC ATG CTG GGC ATC TGG ACC CTC CTA CCT CTG GTT CTT         230
          Met Leu Gly Ile Trp Thr Leu Leu Pro Leu Val Leu
          -16 -15                     -10                  -5

ACG TCT GTT GCT AGA TTA TCG TCC AAA AGT GTT AAT GCC CAA GTG ACT         278
Thr Ser Val Ala Arg Leu Ser Ser Lys Ser Val Asn Ala Gln Val Thr
                1               5                   10

GAC ATC AAC TCC AAG GGA TTG GAA TTG AGG AAG ACT GTT ACT ACA GTT         326
Asp Ile Asn Ser Lys Gly Leu Glu Leu Arg Lys Thr Val Thr Thr Val
            15              20                  25

GAG ACT CAG AAC TTG GAA GGC CTG CAT CAT GAT GGC CAA TTC TGC CAT         374
Glu Thr Gln Asn Leu Glu Gly Leu His His Asp Gly Gln Phe Cys His
        30              35              40

AAG CCC TGT CCT CCA GGT GAA AGG AAA GCT AGG GAC TGC ACA GTC AAT         422
Lys Pro Cys Pro Pro Gly Glu Arg Lys Ala Arg Asp Cys Thr Val Asn
45              50              55                  60

GGG GAT GAA CCA GAC TGC GTG CCC TGC CAA GAA GGG AAG GAG TAC ACA         470
Gly Asp Glu Pro Asp Cys Val Pro Cys Gln Glu Gly Lys Glu Tyr Thr
                65              70              75

GAC AAA GCC CAT TTT TCT TCC AAA TGC AGA AGA TGT AGA TTG TGT GAT         518
Asp Lys Ala His Phe Ser Ser Lys Cys Arg Arg Cys Arg Leu Cys Asp
            80              85              90

GAA GGA CAT GGC TTA GAA GTG GAA ATA AAC TGC ACC CGG ACC CAG AAT         566
Glu Gly His Gly Leu Glu Val Glu Ile Asn Cys Thr Arg Thr Gln Asn
        95              100             105

ACC AAG TGC AGA TGT AAA CCA AAC TTT TTT TGT AAC TCT ACT GTA TGT         614
Thr Lys Cys Arg Cys Lys Pro Asn Phe Phe Cys Asn Ser Thr Val Cys
110             115                 120

GAA CAC TGT GAC CCT TGC ACC AAA TGT GAA CAT GGA ATC ATC AAG GAA         662
Glu His Cys Asp Pro Cys Thr Lys Cys Glu His Gly Ile Ile Lys Glu
125             130             135                 140

TGC ACA CTC ACC AGC AAC ACC AAG TGC AAA GAG GAA GTG AAG AGA AAG         710
Cys Thr Leu Thr Ser Asn Thr Lys Cys Lys Glu Glu Val Lys Arg Lys
                145             150                 155

GAA GTA CAG AAA ACA TGC AGA AAG CAC AGA AAG GAA AAC CAA GGT TCT         758
Glu Val Gln Lys Thr Cys Arg Lys His Arg Lys Glu Asn Gln Gly Ser
                160             165                 170

CAT GAA TCT CCA ACC TTA AAT CCT GAA ACA GTG GCA ATA AAT TTA TCT         806
His Glu Ser Pro Thr Leu Asn Pro Glu Thr Val Ala Ile Asn Leu Ser
            175                 180                 185
```

| | | | | | | | | | | | | | | | | |
|---|---|---|---|---|---|---|---|---|---|---|---|---|---|---|---|---|
| GAT | GTT | GAC | TTG | AGT | AAA | TAT | ATC | ACC | ACT | ATT | GCT | GGA | GTC | ATG | ACA | 854 |
| Asp | Val | Asp | Leu | Ser | Lys | Tyr | Ile | Thr | Thr | Ile | Ala | Gly | Val | Met | Thr | |
| | | | 190 | | | 195 | | | | | 200 | | | | | |
| CTA | AGT | CAA | GTT | AAA | GGC | TTT | GTT | CGA | AAG | AAT | GGT | GTC | AAT | GAA | GCC | 902 |
| Leu | Ser | Gln | Val | Lys | Gly | Phe | Val | Arg | Lys | Asn | Gly | Val | Asn | Glu | Ala | |
| 205 | | | | | 210 | | | | | 215 | | | | | 220 | |
| AAA | ATA | GAT | GAG | ATC | AAG | AAT | GAC | AAT | GTC | CAA | GAC | ACA | GCA | GAA | CAG | 950 |
| Lys | Ile | Asp | Glu | Ile | Lys | Asn | Asp | Asn | Val | Gln | Asp | Thr | Ala | Glu | Gln | |
| | | | | 225 | | | | | 230 | | | | | 235 | | |
| AAA | GTT | CAA | CTG | CTT | CGT | AAT | TGG | CAT | CAA | CTT | CAT | GGA | AAG | AAA | GAA | 998 |
| Lys | Val | Gln | Leu | Leu | Arg | Asn | Trp | His | Gln | Leu | His | Gly | Lys | Lys | Glu | |
| | | | 240 | | | | | 245 | | | | 250 | | | | |
| GCG | TAT | GAC | ACA | TTG | ATT | AAA | GAT | CTC | AAA | AAA | GCC | AAT | CTT | TGT | ACT | 1046 |
| Ala | Tyr | Asp | Thr | Leu | Ile | Lys | Asp | Leu | Lys | Lys | Ala | Asn | Leu | Cys | Thr | |
| | | 255 | | | | | 260 | | | | | 265 | | | | |
| CTT | GCA | GAG | AAA | ATT | CAG | ACT | ATC | ATC | CTC | AAG | GAC | ATT | ACT | AGT | GAC | 1094 |
| Leu | Ala | Glu | Lys | Ile | Gln | Thr | Ile | Ile | Leu | Lys | Asp | Ile | Thr | Ser | Asp | |
| | 270 | | | | | 275 | | | | | 280 | | | | | |
| TCA | GAA | AAT | TCA | AAC | TTC | AGA | AAT | GAA | ATC | CAA | AGC | TTG | GTC | | | 1136 |
| Ser | Glu | Asn | Ser | Asn | Phe | Arg | Asn | Glu | Ile | Gln | Ser | Leu | Val | | | |
| 285 | | | | 290 | | | | | 295 | | | | | | | |

| | | | | |
|---|---|---|---|---|
| TAGAGTGAAA | AACAACAAAT | TCAGTTCTGA | GTATATGCAA | TTAGTGTTTG | AAAAGATTCT | 1196 |
| TAATAGCTGG | CTGTAAATAC | TGCTTGGTTT | TTTACTGGGT | ACATTTATC | ATTTATTAGC | 1256 |
| GCTGAAGAGC | CAACATATTT | GTAGATTTTT | AATATCTCAT | GATTCTGCCT | CCAAGGATGT | 1316 |
| TTAAAATCTA | GTTGGGAAAA | CAAACTTCAT | CAAGAGTAAA | TGCAGTGGCA | TGCTAAGTAC | 1376 |
| CCAAATAGGA | GTGTATGCAG | AGGATGAAAG | ATTAAGATTA | TGCTCTGGCA | TCTAACATAT | 1436 |
| GATTCTGTAG | TATGAATGTA | ATCAGTGTAT | GTTAGTACAA | ATGTCTATCC | ACAGGCTAAC | 1496 |
| CCCACTCTAT | GAATCAATAG | AAGAAGCTAT | GACCTTTGC | TGAAATATCA | GTTACTGAAC | 1556 |
| AGGCAGGCCA | CTTTGCCTCT | AAATTACCTC | TGATAATTCT | AGAGATTTTA | CCATATTTCT | 1616 |
| AAACTTTGTT | TATAACTCTG | AGAAGATCAT | ATTTATGTAA | AGTATATGTA | TTTGAGTGCA | 1676 |
| GAATTTAAAT | AAGGCTCTAC | CTCAAAGACC | TTTGCACAGT | TTATTGGTGT | CATATTATAC | 1736 |
| AATATTTCAA | TTGTGAATTC | ACATAGAAAA | CATTAAATTA | TAATGTTTGA | CTATTATATA | 1796 |
| TGTGTATGCA | TTTTACTGGC | TCAAAACTAC | CTACTTCTTT | CTCAGGCATC | AAAAGCATTT | 1856 |
| TGAGCAGGAG | AGTATTACTA | GAGCTTTGCC | ACCTCTCCAT | TTTTGCCTTG | GTGCTCATCT | 1916 |
| TAATGGCCTA | ATGCACCCCC | AAACATGGAA | ATATCACCAA | AAAATACTTA | ATAGTCCACC | 1976 |
| AAAAGGCAAG | ACTGCCCTTA | GAAATTCTAG | CCTGGTTTGG | AGATACTAAC | TGCTCTCAGA | 2036 |
| GAAAGTAGCT | TTGTGACATG | TCATGAACCC | ATGTTGCAA | TCAAGATGA | TAAAATAGAT | 2096 |
| TCTTATTTTT | CCCCCACCCC | CGAAAATGTT | CAATAATGTC | CCATGTAAAA | CCTGCTACAA | 2156 |
| ATGGCAGCTT | ATACATAGCA | ATGGTAAAAT | CATCATCTGG | ATTTAGGAAT | TGCTCTTGTC | 2216 |
| ATACCCTCAA | GTTTCTAAGA | TTTAAGATTC | TCCTTACTAC | TATCCTACGT | TTAAATATCT | 2276 |
| TTGAAAGTTT | GTATTAAATG | TGAATTTTAA | GAAATAATAT | TTATATTTCT | GTAAATGTAA | 2336 |
| ACTGTGAAGA | TAGTTATAAA | CTGAAGCAGA | TACCTGGAAC | CACCTAAAGA | ACTTCCATTT | 2396 |
| ATGGAGGATT | TTTTTGCCCC | TTGTGTTTGG | AATTATAAAA | TATAGGTAAA | AGTACGTAAT | 2456 |
| TAAATAATGT | TTTTG | | | | | 2471 |

( 2 ) INFORMATION FOR SEQ ID NO:19:

( i ) SEQUENCE CHARACTERISTICS:
        ( A ) LENGTH: 314 amino acids
        ( B ) TYPE: amino acid (D) TOPOLOGY: linear (ii) MOLECULE TYPE: protein (xi) SEQUENCE DESCRIPTION: SEQ ID NO:19:

```
Met Leu Gly Ile Trp Thr Leu Leu Pro Leu Val Leu Thr Ser Val Ala
-16 -15              -10                  -5

Arg Leu Ser Ser Lys Ser Val Asn Ala Gln Val Thr Asp Ile Asn Ser
  1           5                  10                      15

Lys Gly Leu Glu Leu Arg Lys Thr Val Thr Thr Val Glu Thr Gln Asn
             20              25              30

Leu Glu Gly Leu His His Asp Gly Gln Phe Cys His Lys Pro Cys Pro
         35              40                  45

Pro Gly Glu Arg Lys Ala Arg Asp Cys Thr Val Asn Gly Asp Glu Pro
     50              55              60

Asp Cys Val Pro Cys Gln Glu Gly Lys Glu Tyr Thr Asp Lys Ala His
 65              70              75                      80

Phe Ser Ser Lys Cys Arg Arg Cys Arg Leu Cys Asp Glu Gly His Gly
             85              90              95

Leu Glu Val Glu Ile Asn Cys Thr Arg Thr Gln Asn Thr Lys Cys Arg
            100             105             110

Cys Lys Pro Asn Phe Phe Cys Asn Ser Thr Val Cys Glu His Cys Asp
        115             120             125

Pro Cys Thr Lys Cys Glu His Gly Ile Ile Lys Glu Cys Thr Leu Thr
    130             135             140

Ser Asn Thr Lys Cys Lys Glu Val Lys Arg Lys Glu Val Gln Lys
145             150             155             160

Thr Cys Arg Lys His Arg Lys Glu Asn Gln Gly Ser His Glu Ser Pro
            165             170             175

Thr Leu Asn Pro Glu Thr Val Ala Ile Asn Leu Ser Asp Val Asp Leu
        180             185             190

Ser Lys Tyr Ile Thr Thr Ile Ala Gly Val Met Thr Leu Ser Gln Val
        195             200             205

Lys Gly Phe Val Arg Lys Asn Gly Val Asn Glu Ala Lys Ile Asp Glu
    210             215             220

Ile Lys Asn Asp Asn Val Gln Asp Thr Ala Glu Gln Lys Val Gln Leu
225             230             235             240

Leu Arg Asn Trp His Gln Leu His Gly Lys Lys Glu Ala Tyr Asp Thr
            245             250             255

Leu Ile Lys Asp Leu Lys Lys Ala Asn Leu Cys Thr Leu Ala Glu Lys
        260             265             270

Ile Gln Thr Ile Ile Leu Lys Asp Ile Thr Ser Asp Ser Glu Asn Ser
    275             280             285

Asn Phe Arg Asn Glu Ile Gln Ser Leu Val
    290             295
```

(2) INFORMATION FOR SEQ ID NO:20:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO:20:

```
His Leu Pro Cys Pro Pro Gly Glu Arg Lys Ala Arg Asp
 1           5                  10
```

(2) INFORMATION FOR SEQ ID NO:21:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:21:

Asn Leu Gly Trp Leu Cys Leu Leu Leu Leu Pro Ile Pro Leu Ile Val
1               5                   10                  15

(2) INFORMATION FOR SEQ ID NO:22:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:22:

Thr Lys Cys Lys Glu Glu Val Lys Arg Lys Glu Val
1               5                   10